(12) United States Patent
Kusneic et al.

(10) Patent No.: US 10,669,254 B2
(45) Date of Patent: Jun. 2, 2020

(54) PROCESS FOR PREPARING METHOXY METHYL PYRIDINE DICARBOXYLATE

(71) Applicants: Tzurit Kusneic, Lod (IL); Omer Tzor, Kiryat-ono (IL); Avihai Yacovan, Mazkeret Batya (IL)

(72) Inventors: Tzurit Kusneic, Lod (IL); Omer Tzor, Kiryat-ono (IL); Avihai Yacovan, Mazkeret Batya (IL)

(73) Assignee: ADAMA AGAN LTD., Ashdod (IL)

( * ) Notice: Subject to any disclaimer, the term of this patent is extended or adjusted under 35 U.S.C. 154(b) by 0 days.

(21) Appl. No.: 16/462,673

(22) PCT Filed: Nov. 14, 2017

(86) PCT No.: PCT/IB2017/001510
§ 371 (c)(1),
(2) Date: May 21, 2019

(87) PCT Pub. No.: WO2018/091964
PCT Pub. Date: May 24, 2018

(65) Prior Publication Data
US 2019/0276427 A1    Sep. 12, 2019

Related U.S. Application Data

(60) Provisional application No. 62/424,888, filed on Nov. 21, 2016.

(51) Int. Cl.
*C07D 401/04* (2006.01)
*C07D 213/803* (2006.01)

(52) U.S. Cl.
CPC ....... *C07D 401/04* (2013.01); *C07D 213/803* (2013.01)

(58) Field of Classification Search
CPC .................................................. C07D 401/04

USPC .......................................................... 546/274
See application file for complete search history.

(56) References Cited

U.S. PATENT DOCUMENTS 5,288,866 A    2/1994    Strong

FOREIGN PATENT DOCUMENTS

WO    WO 2010/055139 A1    5/2010

OTHER PUBLICATIONS

International Search Report dated Apr. 17, 2018 in connection with PCT International Application No. PCT/IB2017/001510.
Kim, E-H. et al., "Halogenation of Aromatic Methyl Ketones Using Oxone and Sodium Halide", Synthetic Communications, Taylor & Francis inc., Philadelphia, PA, US, vol. 31, No. 23, Jan. 1, 2001, pp. 3627-3632.
Written Opinion of the International Searching Authority dated Apr. 17, 2018 in connection with PCT International Application No. PCT/IB2017/001510.

*Primary Examiner* — Taofiq A Solola
(74) *Attorney, Agent, or Firm* — Gary J. Gershik; Cooper & Dunham LLP

(57) ABSTRACT

The present invention provides a process for preparing a compound of the formula (I):

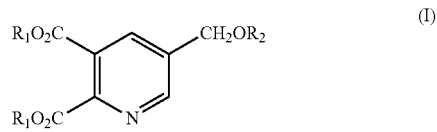

wherein
each occurrence of $R_1$ is a $C_1$-$C_4$ alkyl; and
$R_2$ is $C_1$-$C_4$ alkyl.

20 Claims, No Drawings

PROCESS FOR PREPARING METHOXY METHYL PYRIDINE DICARBOXYLATE

CROSS-REFERENCE TO RELATED APPLICATIONS

This application is a § 371 national stage of PCT International Application No. PCT/IB2017/001510, filed Nov. 14, 2017, which claims the benefit of U.S. Provisional Application No. 62/424,888, filed Nov. 21, 2016, the contents of each of which are hereby incorporated by references into the application.

Throughout this application various publications are referenced. The disclosures of these documents in their entireties are hereby incorporated by reference into this application in order to more fully describe the state of the art to which this invention pertains.

TECHNICAL FIELD

The present subject matter relates to a process for efficient procedure for preparing methoxy methyl pyridine dicarboxylate.

BACKGROUND

Imazamox is a systemic herbicide that functions by inhibiting the acetolactate synthase (ALS) protein in plants. The compound di alkyl-5,6 dicarboxylate-3-alkoxymethyl pyridine of formula (I)

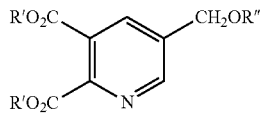

is an important intermediate for preparing the herbicidal active ingredient Imazamox (2-[(RS)-4-isopropyl-4-methyl-5-oxo-2-imidazolin-2-yl]-5-methoxymethylnicotinic acid).

Different manufacturing processes are known from the literature. EP0548532 discloses the reaction of methyl pyridine with halogenating agent to minimize the dihalogenated product and the reaction of ammonium bromide in methanol under nitrogen reflux for 6 hours. U.S. Pat. No. 5,760,239 discloses preparing 2, 3-disubstituted 5-methoxymethyl pyridine by reacting the ammonium bromide with base in presence of an alcohol at temperature of 120-180° C. and under pressure in closed system. WO 2010066669 describes preparing 2, 3 disubstituted 5-methoxymethyl pyridine from trimethyl ammonium bromide, dimethyl ester in methanol/$H_2O$ with base comprising $MOCH_3$, MOH, where the reaction is under pressure in closed vessel at temperature of from 75 to 110° C. WO 2010055139 discloses preparing 2,3-disubstituted 5-pyridylmethyl ammonium bromide from 2, 3 disubstituted 5-pyridylmethyl reacts with bromine followed with trialkyl amine.

However, there is a need to develop a more efficient synthesis pathway by improving the different steps of the process and there is a need to improve each step of the complete reaction in high yield and conversion.

SUMMARY OF THE INVENTION

The present invention provides a process for preparing a compound of the formula (I):

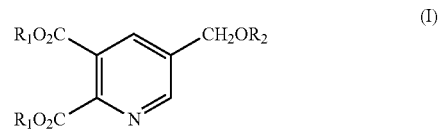

wherein
each occurrence of $R_1$ is a $C_1$-$C_4$ alkyl; and
$R_2$ is $C_1$-$C_4$ alkyl,
comprising the steps of:
(i) reacting a dialkyl-3-methylpyridine-5,6-dicarboxylate with potassium peroxymonosulfate and a halogen metal salt to obtain a mixture comprising the compounds of the formulas IIa, and/or IIb and/or IIc:

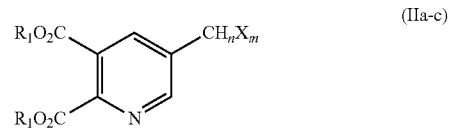

wherein
n=2 and m=1 (IIa), n=1 and m=2 (IIb), or n=0 and m=3 (IIc);
each occurrence of $R_1$ is a $C_1$-$C_4$ alkyl; and
X is a halogen,
(ii) reacting the mixture produced in step (i) with an amine to obtain a compound of the formula (III):

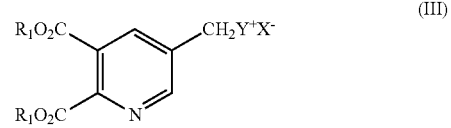

wherein
each occurrence of $R_1$ is a $C_1$-$C_4$ alkyl;
$Y^+$ is

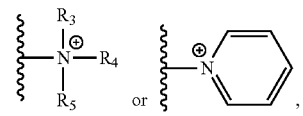

wherein $R_3$, $R_4$ and $R_5$ are each, independently, a $C_1$-$C_6$ alkyl or aryl; and
X is a halogen,
(iii) reacting the product of step (ii) with an alcohol metal base.

The present invention also provides a process for preparing a mixture comprising compounds of the formula IIa and/or IIb and/or IIc:

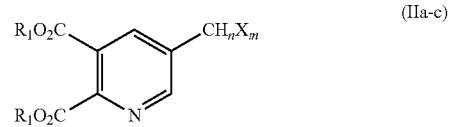

wherein
X is a halogen;
Each occurrence of $R_1$ is $C_1$-$C_4$ alkyl;
n=2 and m=1 (IIa), n=1 and m=2 (IIb) or n=0 and m=3 (IIc), comprising reacting a dialkyl-3-methylpyridine-5,6-dicarboxylate with potassium peroxymonosulfate and a halogen metal salt in the presence of a radical initiator.

The present invention further provides a process for preparing compound of the formula (III):

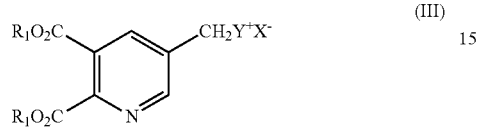
(III)

wherein
each occurrence of $R_1$ is a $C_1$-$C_4$ alkyl;
$Y^+$ is

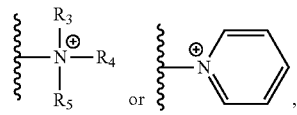, wherein $R_3$, $R_4$ and $R_5$ are each, independently, a $C_1$-$C_6$ alkyl or aryl; and
X is a halogen, comprising reacting a mixture comprising compounds of the formula IIa and/or IIb and/or IIc:

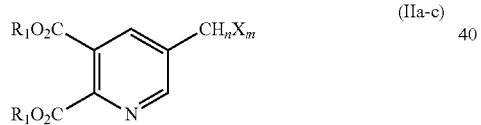
(IIa-c)

wherein
n=2 and m=1 (IIa), n=1 and m=2 (IIb) or n=0 and m=3 (IIc);
each occurrence of $R_1$ is a $C_1$-$C_4$ alkyl; and
X is a halogen, with a dialkylphosphite in presence of an amine so as to therefore obtain the compound of the formula (III).

The present invention also provides a process for preparing a compound of the formula (I):

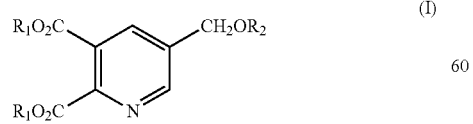
(I)

wherein
Each occurrence of $R_1$ is $C_1$-$C_4$ alkyl;
$R_2$ is $C_1$-$C_4$ alkyl, comprising reacting the compound of formula (III):

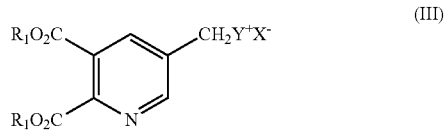
(III)

wherein
each occurrence of $R_1$ is a $C_1$-$C_4$ alkyl;
$Y^+$ is

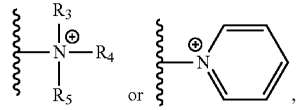, wherein $R_3$, $R_4$ and $R_5$ are each, independently, a $C_1$-$C_6$ alkyl or aryl; and
X is halogen, with an alcohol metal base in the presence of a hydroxide scavenger agent or with an alcohol metal base which was previously treated with a hydroxide scavenger agent.

The present invention yet further provides a process for preparing the compound of the formula

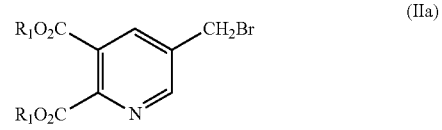
(IIa)

wherein
each occurrence of $R_1$ is a $C_1$-$C_4$ alkyl,
comprising reacting of compounds of formula (IIb-c)

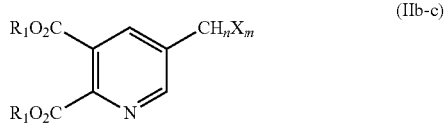
(IIb-c)

wherein
n=1 and m=2 (IIb), or n=0 and m=3 (IIc);
each occurrence of $R_1$ is a $C_1$-$C_4$ alkyl; and
X is a bromine, with a dialkylphosphite in the presence of a base so as to therefore obtain the compound of the formula (IIa).

The present invention provides a process for preparing the compound having the structure:

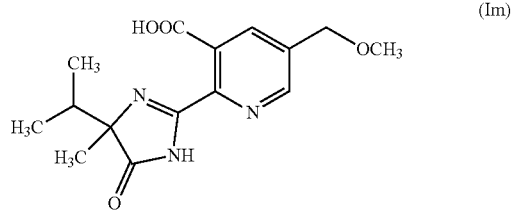 [SMILES: COCc1cnc(C2=NC(C)(C(C)C)C(=O)N2)c(C(=O)O)c1]
(Im)

which comprises converting a dialkyl-3-methylpyridine-5,6-dicarboxylate to a compound having the structure:

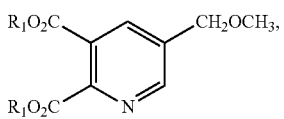

(I)

wherein each occurrence of $R_1$ is $C_1$-$C_4$ alkyl, the improvement in the proves comprising converting the dialkyl-3-methylpyridine-5,6-dicarboxylate to the compound of formula (I) by the process according to any embodiment of the present invention.

DETAILED DESCRIPTION OF THE INVENTION

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of". In each such instance, the terms "comprising," "consisting essentially of," and "consisting of" are intended to have the same meaning as each such term would have when used as the transition phrase of a patent claim.

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, used of the term "about" herein specifically includes ±10% from the indicated values in the range. In addition, the endpoints of all ranges directed to the same component or property herein are inclusive of the endpoints, are independently combinable, and include all intermediate points and ranges.

The present invention to provide a process which is suitable for industrial use, highly efficient, low-cost, environmentally friendly.

The present invention provides a process for preparing a compound of the formula (I):

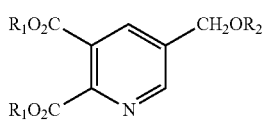

(I)

wherein
each occurrence of $R_1$ is a $C_1$-$C_4$ alkyl; and
$R_2$ is $C_1$-$C_4$ alkyl,
comprising the steps of:
(i) reacting a dialkyl-3-methylpyridine-5,6-dicarboxylate with potassium peroxymonosulfate and a halogen metal salt to obtain a mixture comprising the compounds of the formulas IIa and/or IIb and/or IIc:

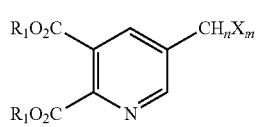

(IIa-c)

wherein
n=2 and m=1 (IIa), n=1 and m=2 (IIb), or n=0 and m=3 (IIc);
each occurrence of $R_1$ is a $C_1$-$C_4$ alkyl; and
X is a halogen,
(ii) reacting the mixture produced in step (i) with an amine to obtain a compound of the formula (III):

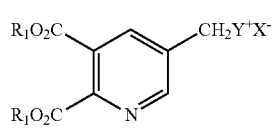

(III)

wherein
each occurrence of $R_1$ is a $C_1$-$C_4$ alkyl;
$Y^+$ is

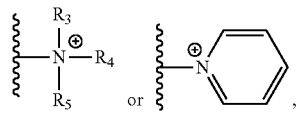

wherein $R_3$, $R_4$ and $R_5$ are each, independently, a $C_1$-$C_6$ alkyl or aryl; and
X is a halogen,
(iii) reacting the product of step (ii) with an alcohol metal base.

In some embodiments, wherein step (i) occurs in the presence of a radical initiator.

In some embodiments, wherein the radical initiator is azobisisobutyronitrile (AIBN).

In some embodiments, wherein the radical initiator is activated by heating the reaction mixture.

In some embodiments, wherein the radical reaction is induced by light.

Light may be visible light or ultraviolet light.

In some embodiments, wherein step (i) is performed in the presence of visible light.

In some embodiments, wherein step (i) is performed in the presence of ultraviolet light.

In some embodiments, wherein when step (i) is conducted in presence of light, compound of the below formula (CPDC) is obtained.

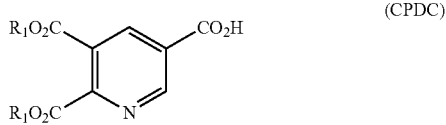

(CPDC)

In some embodiments, the amount of (CPDC) is less than or equal to 1%, or 2%, or 3%, or 4%, or 5%, or 6%, or 7%, 8%, or 9%, or 10% of the product obtained.

In some embodiments, wherein the potassium peroxymonosulfate in step (i) is added to the reaction mixture gradually in two or more portions.

In some embodiments, wherein the reaction is performed in a first suitable solvent.

In some embodiments, wherein the first suitable solvent is dichloromethane, chloroform, 1,2-dichloroethane, perchloroethylene, trichloroethane, chlorobenzene, 2-dichlorobenzene, 3-dichlorobenzene, 4-dichlorobenzene, benzene, carbon tetrachloride or any combination thereof.

In some embodiments, wherein the first suitable solvent is 1,2-dichloroethane.

In some embodiments, the concentration of the potassium peroxymonosulfate, e.g. OXONE®, in step (i) relative to the reaction solution is 1%, or 2%, or 3%, or 4%, or 5%, or 6%, or 7%, or 8%, or 9%, or 10%.

In some embodiments, the concentration of the potassium peroxymonosulfate, e.g. OXONE®, in step (i) relative to the reaction solution is 5%.

In some embodiments, the concentration of the potassium peroxymonosulfate, e.g. OXONE®, in step (i) relative to the reaction solution is 1%.

In some embodiments, the concentration of the potassium peroxymonosulfate, e.g. OXONE®, in step (i) relative to the reaction solution is less than 1%, or 2%, or 3%, or 4%, or 5%, or 6%, or 7%, or 8%, or 9%, or 10%.

In some embodiments, the concentration of the potassium peroxymonosulfate, e.g. OXONE®, in step (i) relative to the reaction solution is less than 5%.

In some embodiments, the concentration of the potassium peroxymonosulfate, e.g. OXONE®, in step (i) relative to the reaction solution is less than 1%.

In some embodiments, the concentration of the potassium peroxymonosulfate, e.g. OXONE®, in step (i) relative to the reaction solution is between 4% and 6%.

In some embodiments, the concentration of the potassium peroxymonosulfate, e.g. OXONE®, in step (i) relative to the reaction solution is 0.5% and 1.5%.

In some embodiments, the concentration of the dialkyl-3-methylpyridine-5,6-dicarboxylate in step (i) relative to the reaction solution is less than or equal to 1%, or 2%, or 3%, or 4%, or 5%, or 6%, or 7%, or 8%, or 9%, or 10%.

In some embodiments, the concentration of the dialkyl-3-methylpyridine-5,6-dicarboxylate in step (i) relative to the reaction solution is less than 5%.

In some embodiments, the concentration of the dialkyl-3-methylpyridine-5,6-dicarboxylate in step (i) relative to the reaction solution is less than 1%.

In some embodiments, the concentration of the halogen metal salt in step (i) relative to the reaction solution is less than or equal to 1%, or 2%, or 3%, or 4%, or 5%, or 6%, or 7%, or 8%, or 9%, or 10%.

In some embodiments, the concentration of the halogen metal salt in step (i) relative to the reaction solution is 5%.

In step (i) In some embodiments, the concentration of the halogen metal salt relative to the reaction solution is 1%.

In some embodiments, the concentration of the halogen metal salt relative to the reaction solution is 1% or less, or 2% or less, or 3% or less, or 4% or less, or 5% or less, or 6% or less, or 7% or less, or 8% or less, or 9% or less, or 10% or less.

In some embodiments, the concentration of the halogen metal salt in step (i) relative to the reaction solution is less than 5%.

In step (i) In some embodiments, the concentration of the halogen metal salt relative to the reaction solution is less than 1%.

In some embodiments, the concentration of the halogen metal salt in step (i) relative to the reaction solution between 4% and 6%.

In some embodiments, the concentration of the halogen metal salt in step (i) relative to the reaction solution between 0.5% and 1.5%.

In some embodiments, wherein in step (ii) the halogenated products of step (i) are reacted with the amine in the presence of diethylphosphite.

In some embodiments, wherein in step (ii) the dihalogenated and trihalogenated products IIb and IIc of step (i) react with the diethylphosphite in presence of non-nucleophilic base prior to reaction with the amine.

In some embodiments, wherein in step (ii) the dihalogenated and trihalogenated products IIb and IIc of step (i) are converted to the monohalogenated product IIa prior to reaction with the amine.

In some embodiments, wherein the amine in step (ii) is trimethylamine.

In some embodiments, the amine is a gas.

In some embodiments, the amine is a liquid or a solution of a gaseous amine.

In some embodiments, wherein the metal in step (i) and/or (iii) is alkali or earth alkaline.

In some embodiments, wherein the halogen X is bromide, chloride, fluoride or iodide.

In some embodiments, wherein the halogen metal salt in step (i) is sodium bromide.

In some embodiments, wherein the alcohol in step (iii) is methanol.

In some embodiments, wherein step (iii) is carried out in the presence of a hydroxide scavenger agent.

In some embodiments, wherein compound (iii) is dried prior to the reaction with alcohol metal base.

In some embodiments, wherein compound (iii) is treated with dehydrating agents and/or materials prior to the reaction with alcohol metal base.

Dehydrating agents and/or materials include, but are not limited to, trialkylorthoformates, highly hygroscopic inorganic salts, molecular sieves and combination thereof.

Trialkylorthoformates include, but are not limited to, trimethylorthoformate and triethylorthoformate.

In some embodiments, the product of step (ii) is treated with a dehydrating agent in the presence of acid. Examples of acid include organic acid or inorganic acid.

Organic acids include, but are not limited to, p-toluenesulfonic acid, benzene sulfonic acid, methanesulfonic acid, trifluoroacetic acid and acetic acid.

Inorganic acids include, but are not limited to, sulfuric acid, phosphoric acid and hydrochloric acid.

In some embodiments of the process, the reaction is carried out under atmospheric pressure or under excess pressure of up to 6 bar.

In some embodiments, wherein the hydroxide scavenger agent is methyl acetate.

In some embodiments, wherein the hydroxide scavenger agent is ethyl acetate.

In some embodiments, wherein the alcohol metal base is treated with a hydroxide scavenger agent prior to the reaction with compound (III).

In some embodiments, the above step (i) produces a mixture of the following compounds:

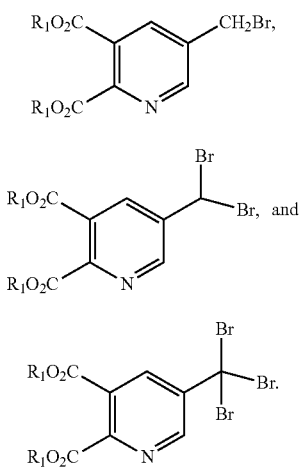

In some embodiments, wherein the compound produced has the structure:

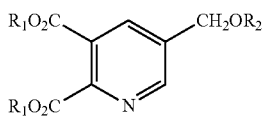

wherein each $R_1$ and $R_2$ are methyl.

In some embodiments, wherein the compound produced has the structure:

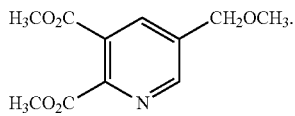

In some embodiments, wherein the potassium peroxymonosulfate source is a triple salt with the formula $KHSO_5 \cdot 0.5KHSO_4 \cdot 0.5K_2SO_4$.

In some embodiments, the potassium peroxymonosulfate is OXONE®.

In some embodiments of the above process, further comprising a step (i) (a) after step (i) and prior to step (ii) wherein the mixture comprising the compounds IIa-c of step (i) are reacted with a dialkylphosphite so as to therefore obtain the compound of the formula IIa.

In some embodiments of the above process, further comprising a step (i) (a) after step (i) and prior to step (ii) wherein the mixture comprising the compounds IIa-c of step (i) are reacted with a dialkylphosphite so as to therefore covert the compound of the formula IIb-c to the compound of the formula IIa.

The present invention also provides a process for preparing a mixture comprising compounds of the formula IIa and/or IIb and/or IIc:

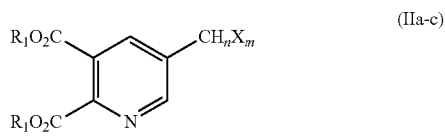

wherein
X is a halogen;
Each occurrence of $R_1$ is $C_1$-$C_4$ alkyl;
n=2 and m=1 (IIa), n=1 and m=2 (IIb) or n=0 and m=3 (IIc), comprising reacting a dialkyl-3-methylpyridine-5,6-dicarboxylate with potassium peroxymonosulfate and a halogen metal salt in the presence of a radical initiator.

In some embodiments, wherein the radical initiator is azobisisobutyronitrile (AIBN).

In some embodiments, wherein the radical initiator is activated by heating the reaction mixture.

In some embodiments, wherein the reaction is induced by light. Light may be visible and/or ultraviolet light.

In some embodiments, wherein the reaction is performed in the presence of visible light.

In some embodiments, wherein the reaction is performed in the presence of ultraviolet light.

In some embodiments, wherein the potassium peroxymonosulfate is added to the reaction mixture gradually in two or more portions.

In some embodiments, wherein the reaction is performed in a first suitable solvent.

In some embodiments, wherein the first suitable solvent is dichloromethane, chloroform, 1,2-dichloroethane, perchloroethylene, trichloroethane, chlorobenzene, 2-dichlorobenzene, 3-dichlorobenzene, 4-dichlorobenzene, benzene, carbon tetrachloride or any combination thereof.

In some embodiments, wherein the first suitable solvent is 1,2-dichloroethane.

In some embodiments, the concentration of the potassium peroxymonosulfate, e.g. OXONE®, relative to the reaction solution is 1%, or 2%, or 3%, or 4%, or 5%, or 6%, or 7%, or 8%, or 9%, or 10%.

In some embodiments, the concentration of the potassium peroxymonosulfate, e.g. OXONE®, relative to the reaction solution is 1% or less, or 2% or less, or 3% or less, or 4% or less, or 5% or less, or 6% or less, or 7% or less, or 8% or less, or 9% or less, or 10% or less.

In some embodiments, the concentration of the potassium peroxymonosulfate, e.g. OXONE®, relative to the reaction solution is 5%.

In some embodiments, the concentration of the potassium peroxymonosulfate, e.g. OXONE®, relative to the reaction solution is between 4% and 6%.

In some embodiments, the concentration of the potassium peroxymonosulfate, e.g. OXONE®, relative to the reaction solution is 1%.

In some embodiments, the concentration of the potassium peroxymonosulfate, e.g. OXONE®, relative to the reaction solution is between 0.5% and 1.5%.

In some embodiments, the concentration of the dialkyl-3-methylpyridine-5,6-dicarboxylate relative to the reaction solution is less than or equal to 1%, or 2%, or 3%, or 4%, or 5%, or 6%, or 7%, or 8%, or 9%, or 10%.

In some embodiments, the concentration of the dialkyl-3-methylpyridine-5,6-dicarboxylate relative to the reaction solution is less than 5%.

In some embodiments, the concentration of the dialkyl-3-methylpyridine-5,6-dicarboxylate relative to the reaction solution is less than 1%.

In some embodiments, the concentration of the halogen metal salt relative to the reaction solution is 1%, or 2%, or 3%, or 4%, or 5%, or 6%, or 7%, or 8%, or 9%, or 10%.

In some embodiments, the concentration of the halogen metal salt relative to the reaction solution is 1% or less, or 2% or less, or 3% or less, or 4% or less, or 5% or less, or 6% or less, or 7% or less, or 8% or less, or 9% or less, or 10% or less.

In some embodiments, the concentration of the halogen metal salt relative to the reaction solution is 5%.

In some embodiments, the concentration of the halogen metal salt relative to the reaction solution is 1%.

In some embodiments, the concentration of the halogen metal salt relative to the reaction solution between 4% and 6%.

In some embodiments, the concentration of the halogen metal salt relative to the reaction solution between 0.5% and 1.5%.

In some embodiments, wherein the metal is alkali or earth alkaline.

In some embodiments, wherein the halogen is bromide, chloride, fluoride or iodide.

In some embodiments, wherein the halogen metal salt is sodium bromide.

In some embodiments, wherein the halogen metal salt is sodium chloride, sodium iodide or potassium bromide.

In some embodiments, wherein the potassium peroxymonosulfate source is a triple salt with the formula $KHSO_5 \cdot 0.5 KHSO_4 \cdot 0.5 K_2SO_4$.

In some embodiments, the potassium peroxymonosulfate is OXONE®.

In some embodiments, the above process produces a mixture of the following compounds:

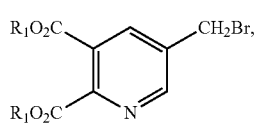
(IIa)

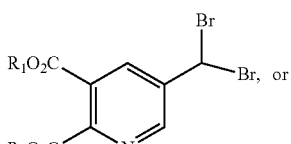
(IIb)

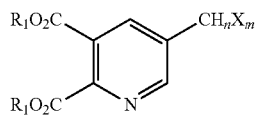
(IIc)

In some embodiment, the mixture obtained from the reaction of dialkyl-3-methylpyridine-5,6-dicarboxylate with potassium peroxymonosulfate and a halogen metal salt comprises compounds of the formula (IIa-b).

In some embodiment, the mixture obtained from the reaction of dialkyl-3-methylpyridine-5,6-dicarboxylate with potassium peroxymonosulfate and a halogen metal salt comprises the compounds of the formula (IIa-c).

In some embodiments, wherein when the reaction is conducted in presence of light, compound of the below formula (CPDC) is obtained.

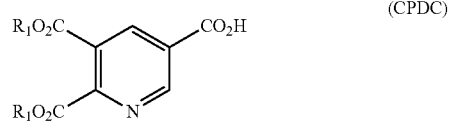
(CPDC)

In some embodiments, the amount of (CPDC) is less than or equal to 1%, or 2%, or 3%, or 4%, or 5%, or 6%, or 7%, 8%, or 9%, or 10% of the product obtained.

In some embodiments, the combined percentage of IIa and IIb produced is greater than 90%.

In some embodiments, the combined percentage of IIa and IIb and IIc produced is greater than 90%.

The present invention further provides a process for preparing compound of the formula (III):

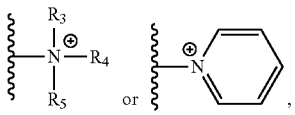
(III)

wherein
each occurrence of $R_1$ is a $C_1$-$C_4$ alkyl; $Y^+$ is $$\begin{array}{c} R_3 \\ | \\ -N^\oplus - R_4 \\ | \\ R_5 \end{array} \quad \text{or} \quad -N^\oplus\diagdown\diagup ,$$

wherein $R_3$, $R_4$ and $R_5$ are each, independently, a $C_1$-$C_6$ alkyl or aryl; and
X is a halogen,
comprising reacting a mixture comprising the compounds of the formula IIa and/or IIb and/or IIc:

$$R_1O_2C\diagdown\diagup\diagdown CH_nX_m \atop R_1O_2C\diagup N \diagdown$$
(IIa-c)

wherein
n=2 and m=1 (IIa), n=1 and m=2 (IIb) or n=0 and m=3 (IIc);
each occurrence of $R_1$ is a $C_1$-$C_4$ alkyl; and
X is a halogen,
with a dialkylphosphite in presence of an amine so as to therefore obtain the compound of the formula (III).

In some embodiments, the amine is an organic amine.
In some embodiments, the amine is a nucleophilic amine.
In some embodiments, the amine is a non-nucleophilic amine.
In some embodiments, the amine is selected form the group consisting of trimethyl amine, triethyl amine, and pyridine.

In some embodiments, wherein amine is selected form the group consisting of tert-butyl dimethyl amine, isobutyl dimethyl amine.

In some embodiments, the amine is a gas.

In some embodiments, the amine is a liquid or a solution of a gaseous amine.

In some embodiments, wherein the process is conducted in one pot reaction.

In some embodiments, wherein the dihalogenated and trihalogenated compounds IIb and IIc react with the diethylphosphite prior to reaction with the amine in the presence of non-nucleophilic base.

In some embodiments, wherein the dihalogenated and trihalogenated compounds IIb and IIc are converted to the monohalogenated product IIa prior to reaction with the amine in the presence of none nucleophilic base.

The present invention further provides a process for preparing a compound of the formula (I):

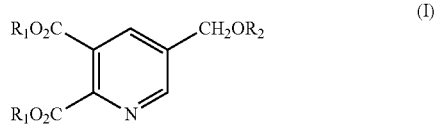

wherein,
Each occurrence of $R_1$ is $C_1$-$C_4$ alkyl;
$R_2$ is $C_1$-$C_4$ alkyl;
comprising reacting the compound of formula (III):

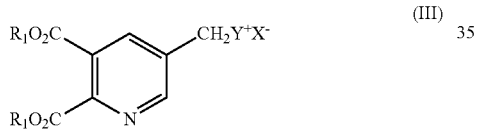

wherein
each occurrence of $R_1$ is a $C_1$-$C_4$ alkyl;
$Y^+$ is

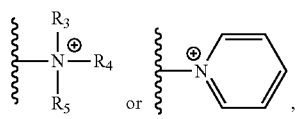

wherein $R_3$, $R_4$ and $R_5$ are each, independently, a $C_1$-$C_6$ alkyl or aryl; and
X is halogen,
with an alcohol metal base in the presence of a hydroxide scavenger agent or with an alcohol metal base which was previously treated with a hydroxide scavenger agent.

In some embodiments, wherein compound (iii) is dried prior to the reaction with alcohol metal base.

In some embodiments, wherein compound (iii) is treated with dehydrating agents and/or materials prior to the reaction with alcohol metal base.

Dehydrating agents and/or materials include, but are not limited to, trialkylorthoformates, highly hygroscopic inorganic salts, molecular sieves and combination thereof.

Trialkylorthoformates include, but are not limited to, trimethylorthoformate and triethylorthoformate.

In some embodiments, the product of step (ii) is treated with a dehydrating agent in the presence of acid. Examples of acid include organic acid or inorganic acid.

Organic acids include, but are not limited to, p-toluenesulfonic acid, benzene sulfonic acid, methanesulfonic acid, trifluoroacetic acid and acetic acid.

Inorganic acids include, but are not limited to, sulfuric acid, phosphoric acid and hydrochloric acid.

In some embodiments of the process, the reaction is carried out under atmospheric pressure or under excess pressure of up to 6 bar.

In some embodiments, wherein the metal is alkali or earth alkaline.

In some embodiments, wherein the alcohol is methanol.

In some embodiments, wherein the alcohol is ethanol.

In some embodiments, wherein the hydroxide scavenger agent is methyl acetate.

In some embodiments, wherein the hydroxide scavenger agent is ethyl acetate.

In some embodiments, wherein the compound of formula (III) is reacted with an alcohol metal base in the presence of a hydroxide scavenger agent.

In some embodiments, wherein the compound of formula (III) is reacted with an alcohol metal base which was previously treated with a hydroxide scavenger agent.

The present invention further provides a process for preparing the compound of the formula:

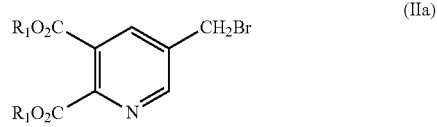

wherein
each occurrence of $R_1$ is a $C_1$-$C_4$ alkyl,
comprising reacting the of compound of formula (IIb-c)

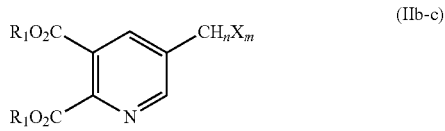

wherein
n=1 and m=2 (IIb) or n=0 and m=3 (IIc);
each occurrence of $R_1$ is a $C_1$-$C_4$ alkyl; and
X is a bromine,
with a dialkylphosphite so as to therefore obtain the compound of the formula (IIa).

In some embodiments, wherein the process, i.e. steps (i), (ii) and (iii), is conducted in one pot.

In some embodiments, the compound of the formula (I) has the structure:

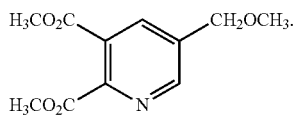

In some embodiments, the compound of the formulas (IIa-c) have the structures:

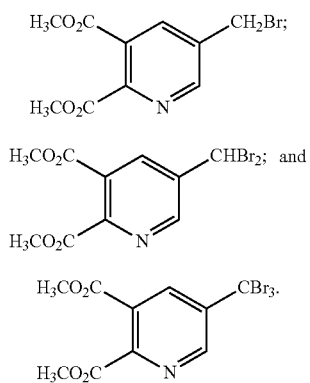

In some embodiments, the compound of the formula (III) has the structure:

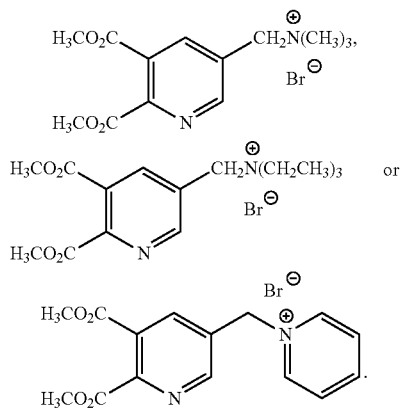

In some embodiments, the reaction of the 3-methylpyridine 5,6-dialkyl dicarboxylate with potassium peroxymonosulfate OXONE® is carried out in solvent.

Potassium peroxymonosulfate is used as an oxidizing agent and is commercially available from DuPont under the trade name OXONE® as a component of a triple salt with the formula $KHSO_5 \cdot 0.5KHSO_4 \cdot 0.5K_2SO_4$. In some embodiments, the potassium peroxymonosulfate source is OXONE®.

In some embodiments, OXONE® refers to solution of $KHSO_5 \cdot 0.5KHSO_4 \cdot 0.5K_2SO_4$ in water. The concentration of OXONE® may be, but is not limited to, 10%, 20%, 30%, 40% or 50%.

In some embodiments, the concentration of the OXONE® in water is 19%.

In some embodiments, the concentration of the OXONE® in water is 25%.

In some embodiments, the concentration of the potassium peroxymonosulfate, e.g. OXONE®, relative to the reaction solution is 1%, or 2%, or 3%, or 4%, or 5%, or 6%, or 7%, or 8%, or 9%, or 10%.

In some embodiments, the concentration of the potassium peroxymonosulfate, e.g. OXONE®, relative to the reaction solution is 5%. In some embodiments, the concentration of the potassium peroxymonosulfate, e.g. OXONE®, relative to the reaction solution is 1%.

In some embodiments, the concentration of the dialkyl-3-methylpyridine-5,6-dicarboxylate relative to the reaction solution is less than 1%, or 2%, or 3%, or 4%, or 5%, or 6%, or 7%, or 8%, or 9%, or 10%.

In some embodiments, the concentration of the dialkyl-3-methylpyridine-5,6-dicarboxylate relative to the reaction solution is less than 5%.

In some embodiments, the concentration of the dialkyl-3-methylpyridine-5,6-dicarboxylate relative to the reaction solution is less than 1%.

In some embodiments, the concentration of the halogen metal salt relative to the reaction solution is 1%, or 2%, or 3%, or 4%, or 5%, or 6%, or 7%, or 8%, or 9%, or 10%.

In some embodiments, the concentration of the halogen metal salt relative to the reaction solution is 5%. In some embodiments, the concentration of the halogen metal salt relative to the reaction solution is 1%.

In some embodiments of any of the above bromination reactions, the solvent is a non-polar solvent.

In some embodiments, the non-polar solvent may include, but is not limited to, dichloromethane, chloroform, 1,2-dichloroethane, perchloroethylene, trichloroethane, chlorobenzene, 2-dichlorobenzne, 3-dichlorobenzene, 4-dichlorobenzene, benzene, carbonbtetrachloride or any combination thereof.

In some embodiments, the molar ratio of the potassium peroxymonosulfate, e.g. OXONE®, to the pyridine substrate is from about 0.7:1.0 to about 3.5:1.0.

In some embodiments, the molar ratio of the potassium peroxymonosulfate, e.g. OXONE®, to the pyridine substrate is 0.3:1.0, or 0.7:1.0, or 1.1:1.0, or 1.5:1.0, or 2.0:1.0, or 2.5:1.0, or 3.0:1.0, or 3.5:1.0.

In some embodiments, the molar ratio of the potassium peroxymonosulfate, e.g. OXONE®, to the pyridine substrate is 0.37:1.0.

In some embodiments, the above molar ratios are maintained as each portion of OXONE® is added.

In some embodiments, the total amount of the potassium peroxymonosulfate, e.g. OXONE®, is added in at least two portions, three portions, four portions, five portions, six portions, seven portions, eight portions, nine portions or ten portions.

In some embodiments, the total amount of halogen metal salt is added in at least two portions, three portions, four portions, five portions, six portions, seven portions, eight portions, nine portions or ten portions.

In some embodiments, the reaction with light and is carried out in absence of a radical initiator.

In some embodiments, the reaction with light and is carried out in absence of a radical initiator and the total amount of the potassium peroxymonosulfate, e.g. OXONE®, is added in one portion.

In some embodiments, reaction is carried out in the presence of a radical initiator.

In some embodiments, reaction is carried out in the presence of a radical initiator and the total amount of the potassium peroxymonosulfate, e.g. OXONE®, is added in one portion.

In some embodiments, reaction with light and is carried out in absence of a radical initiator and the total amount of halogen metal salt is added in one portion.

In some embodiments, reaction which is carried out in presence of initiator and the total amount of halogen metal salt is added in one portion.

In some embodiments, the molar ratio of the halogen metal salt to the pyridine substrate is from about 0.3:1.0 to about 3.5:1.0.

In some embodiments, the molar ratio of the halogen metal salt to the pyridine substrate is from about 0.7:1.0 to about 3.5:1.0.

In some embodiments, the molar ratio of halogen metal salt to the pyridine substrate is 0.41:1.0.

In some embodiments, the above molar ratios are maintained as each portion of halogen metal salt is added.

In some embodiments, the molar ratio of halogen metal salt to the pyridine substrate is 0.7:1.0, or 1.1:1.0, or 1.5:1.0, or 2.0:1.0, or 2.5:1.0, or 3.0:1.0, or 3.5:1.0.

In some embodiments, the total amount of halogen metal salt is added in at last two portions, three portions, four portions, five portions, six portions, seven portions, eight portions, nine portions or ten portions.

In some embodiments of any of the above bromination reactions, the reaction is carried out at a pH less than 5, or less than 4.5, or less than 4, or less than 3.5, or less than 3, or less than 2.5, or less than 2, or less than 1.5, or less than 1.0, or less than 0.5.

In some embodiments of any of the above bromination reactions, the reaction is carried out at a pH between about 1.0 to 2.0.

In some embodiments of any of the above bromination reactions, the concentration of the potassium peroxymonosulfate, e.g. OXONE®, or dialkyl-3-methylpyridine-5,6-dicarboxylate and/or the halogen metal salt in the reaction solution is less than 10%, or less than 9%, or less than 8%, or less than 7%, or less than 6%, or less than 5%, or less than 4%, or less than 3%, or less than 2%, or less than 1%, or less than 0.75%, or less than 0.5%, or less than 0.2%, or less than 0.1%.

In some embodiments, the concentration of the potassium peroxymonosulfate, e.g. OXONE®, or dialkyl-3-methylpyridine-5,6-dicarboxylate and/or the halogen metal salt in the reaction solution is maintained throughout the reaction at less than 10%, or less than 9%, or less than 8%, or less than 7%, or less than 6%, or less than 5%, or less than 4%, or less than 3%, or less than 2%, or less than 1%, or less than 0.75%, or less than 0.5%, or less than 0.2%, or less than 0.1%.

In some embodiments, the concentration of the potassium peroxymonosulfate, e.g. OXONE®, or dialkyl-3-methylpyridine-5,6-dicarboxylate and/or the halogen metal salt in the reaction solution is maintained throughout the reaction at around 1%, 2% or 5%.

In some embodiments, the reaction of 3-methylpyridine 5,6-dialkyl dicarboxylate with the potassium peroxymonosulfate, e.g. OXONE®, and halogens metal salt is carried out in a continuous manner, i.e. the potassium peroxymonosulfate, e.g. OXONE®, is added slowly and wherein the concentration of the potassium peroxymonosulfate, e.g. OXONE®, or dialkyl-3-methylpyridine-5,6-dicarboxylate is not more than 1%, 2% or 5% during the entire reaction time.

In some embodiments of any of the above bromination reactions, the concentration of the potassium peroxymonosulfate, e.g. OXONE®, in the reaction water phase is less than 10%, or less than 9%, or less than 8%, or less than 7%, or less than 6%, or less than 5%, or less than 4%, or less than 3%, or less than 2%, or less than 1%, or less than 0.75%, or less than 0.5%, or less than 0.2%, or less than 0.1%.

In some embodiments of any of the above bromination reactions, the concentration of the potassium peroxymonosulfate, e.g. OXONE®, or dialkyl-3-methylpyridine-5,6-dicarboxylate in the reaction solution is less than 10%, or less than 9%, or less than 8%, or less than 7%, or less than 6%, or less than 5%, or less than 4%, or less than 3%, or less than 2%, or less than 1%, or less than 0.75%, or less than 0.5%, or less than 0.2%, or less than 0.1%.

In some embodiments of any of the above bromination reactions, the concentration of the potassium peroxymonosulfate, e.g. OXONE®, and/or dialkyl-3-methylpyridine-5,6-dicarboxylate and/or halogen metal salt in the reaction solvent is less than 10%, or less than 9%, or less than 8%, or less than 7%, or less than 6%, or less than 5%, or less than 4%, or less than 3%, or less than 2%, or less than 1%, or less than 0.75%, or less than 0.5%, or less than 0.2%, or less than 0.1%.

In some embodiments, the potassium peroxymonosulfate, e.g. OXONE®, is added gradually to the reaction vessel and/or reactor in one or more portions.

In some embodiments, the halogen metal salt is added gradually to the reaction vessel and/or reactor in one or more portions.

In some embodiments, the metal halogen salt is added gradually to the reaction vessel and/or reactor in one or more portions.

In some embodiments, the potassium peroxymonosulfate, e.g. OXONE®, is added dropwise to the reaction vessel and/or reactor.

In some embodiments, the metal halogen salt is added dropwise to the reaction vessel and/or reactor.

In some embodiments, the potassium peroxymonosulfate, e.g. OXONE®, is added to the reaction solution in 1 to 9 portions.

In some embodiments, the halogen metal salt is added to the reaction solution in 1 to 9 portions.

In some embodiments of any of the above bromination reactions, the reaction is conducted at a temperature between 60-80° C. In some embodiments of any of the above bromination reactions, the reaction is carried out in presence of radical initiator.

The radical initiator refers to, but is not limited to, inorganic peroxides, organic peroxides and azo initiators.

Examples of azo initiators may include, but are not limited to, 2,2'-Azobis(2-methylpropionitrile) (AIBN); 2,2'-Azobis(2-methylbutyronitrile) (VAZO67); and 1,1'-Azobis(cyclohexanecarbonitrile) (VAZO88).

Examples of organic peroxide may include, but are not limited to, tert-butyl hydrogen peroxide and benzoyl peroxide.

Examples of inorganic peroxide may include, but are not limited to, ammonium persulfate and sodium persulfate In some embodiments, the metal is an alkaline metal or an earth alkaline metal.

In some embodiments, the halogen is bromide, chloride, iodide or fluoride.

In some embodiments, the yield of the bromination reaction is more than 60%, 70%, 80%, or 90%.

In some embodiments, the yield of the monobromo product (IIa) of the bromination reaction is more than 40%.

In some embodiments, the yield of the dibromo product (IIb) bromination reaction is more than 40%.

In some embodiments, the yield of the tribromo product (IIc) bromination reaction is less than 5%.

In some embodiment the conversion to product of the reaction 3-methylpyridine 5, 6-dialkyl dicarboxylate with OXONE® and halogens metal salt is at least 99.9%.

In some embodiment the conversion to product of the reaction 3-methylpyridine 5, 6-dialkyl dicarboxylate with OXONE® and halogens metal salt is at least 95%.

In some embodiment the conversion to product of the reaction 3-methylpyridine 5, 6-dialkyl dicarboxylate with OXONE® and halogens metal salt is at least 90%.

In some embodiment the conversion to product IIa of the reaction 3-methylpyridine 5, 6-dialkyl dicarboxylate with OXONE® and halogens metal salt is at least 40%.

In some embodiment the conversion to product IIb of the reaction 3-methylpyridine 5, 6-dialkyl dicarboxylate with OXONE® and halogens metal salt is at least 40%.

Amine may refer to a nucleophilic amine or non-nucleophilic amine. In some embodiments, the nucleophilic amine refers to, but is not limited to, trimethyl amine, triethyl amine or pyridine. Examples of non-nucleophilic amines may include, but are not limited to, ethyl diisopropyl amine.

In some embodiments, the mixture comprising the compounds of the formula IIb and/or IIc reacts with dialkylphosphite in presence of an amine.

The dialkylphosphite refers to, but is not limited, to diethylphosphite (DEP).

In some embodiments, the mixture comprising the compounds of formula IIb and/or IIc reacts with the dialkylphosphite in presence of a nucleophilic amine, obtaining the compound (IIa) which is reacted with nucleophilic amine to obtain compound (III) In some embodiments, the mixture comprising the compounds of formula (IIb and/or IIc) reacts with the dialkylphosphite in presence of trimethyl amine, obtaining the compound (IIa) which is reacted with nucleophilic amine to obtain compound (III)

In some embodiments, compound (IIa) is obtained prior to reaction of the nucleophilic amine.

In some embodiments, the compound (IIa) is obtained prior to the reaction with amine by reaction with dialkylphosphite in presence of non-nucleophilic amine.

In some embodiments, wherein the nucleophilic amine is selected form group consisting of trimethyl amine, triethyl amine, and pyridine.

In some embodiments, wherein the non-nucleophilic amine is selected form group consisting of tert-butyl dimethyl amine, isobutyl dimethyl amine.

In one embodiment, wherein the nucleophilic amine is triethyl amine.

In some embodiments, the amine is a gas.

In some embodiments, the amine is a liquid or a solution of a gaseous amine.

In some embodiments, the reaction of the mixture comprising the compounds of formula Iib and/or IIc with amine and dialkylphosphite is a one-pot process.

In some embodiments, the reaction of compounds of formula IIb and/or IIc with amine and dialkylphosphite is a one pot process.

In some embodiments, the mixture comprising the compounds of formula IIb and/or IIc are reacted with the diethylphosphite prior to reaction of IIa with the amine and the product IIa is not isolated prior to reaction with the amine.

In some embodiments, the mixture comprising the compounds of formula IIa and/or IIb and/or IIc is reacted with the diethylphosphite prior to reaction of the IIa portion with the amine.

In some embodiments, the mixture comprising the compounds of formula IIa and/or IIb and/or IIc is reacted with the diethylphosphite prior to reaction of the IIa portion with the amine to increase the amount of IIa, and the product IIa is not isolated prior to reaction with the amine.

In some embodiments, compound IIa is obtained by reacting compound IIb and/or IIc with dialkylphosphite in presence of amine.

In some embodiments, reaction of the mixture comprising compounds IIa and/or IIb and/or IIc with amine is carried out in presence of solvent.

In some embodiments, reaction of compound (IIa) with amine is carried out in presence of solvent.

In some embodiments, the mixture comprising compounds IIa and/or IIb and/or IIc is reacted with dialkylphosphite in presence of amine to convert any present amount of IIb and IIc to a pure compound IIa prior to formation of the tetraalkylammonium salt.

In some embodiments the amination reaction, the reaction is carried out in presence of solvent.

In some embodiment, reaction of compound (III) with alcohol metal base is carried out in presence of solvent.

In some embodiments, reaction of compound (III) with alcohol metal base is carried out in presence of the alcohol solvent.

Solvent includes, but is not limited to, dichloromethane, chloroform, 1,2-dichloroethane, perchloroethylene, trichloroethane, chlorobenzene, 2-dichlorobenzne, 3-dichlorobenzene, 4-dichlorobenzene, toluene, xylene, methanol, ethanol, 2-propanol or acetonitrile, benzene, carbon tetrachloride or any combination thereof.

In some embodiments of any of the above amination reactions, the reaction is carried out at a temperature between about 0° C. to 25° C.

In some embodiments of any of the above amination reactions, the reaction is carried out at a temperature of about 0° C., 10° C., 20° C., 30° C., 40° C., 50° C., 60° C., 70° C., 80° C., 90° C. or 100° C.

In some embodiments, the reaction of compound of formula (III) with alcohol metal base is carried out in the presence of hydroxide scavenger agent.

In some embodiments, the reaction of compound of formula (III) with alcohol metal base is carried out in presence of solvent. In some embodiments, the solvent is an alcohol solvent.

Solvent refers to, but is not limited to, methanol or ethanol.

In some embodiments, the reaction of compound of formula (III) with alcohol metal base is carried out under anhydrous conditions.

In some embodiments, the reaction of compound of formula (III) with alcohol metal base is carried out in nitrogen atmosphere.

In some embodiments, the reaction of compound of formula (III) with alcohol metal base is carried out in argon atmosphere.

In some embodiments, the solvent is dried prior to the reaction with the alcohol metal base.

The hydroxide scavenger agent refers to, but is not limited to, methyl acetate, ethyl acetate.

The metal of the alcohol metal base may be alkaline or earth alkaline metal.

The alcohol of the alcohol metal base may be methanol, ethanol or phenol.

Alkaline refers to, but is not limited to, sodium or potassium.

Earth alkaline refers to, but is not limited to, magnesium.

In some embodiment, the reaction of compound of formula (III) with alcohol metal base is carried out at a temperature of 50-90° C.

Isolation of compound (I) to (III) can be archived by standard processes known to one skilled in the art.

The process described herein is advantageous in that it provides the desired product in a higher yield with less rigorous purification.

The process described herein is advantageous in that it provides the desired product in a higher yield with less time consuming, less costly and more environmentally efficient purification.

The process described herein is advantageous in that it provides the desired product with reduced cost.

The process described herein is advantageous in that it avoids the need for toxic reagents, which are not particularly desirable for industrial implementation due to the hazards associated with such reagents.

The process described herein is also advantageous in that it may be performed in one-pot.

Step (i):

In the present invention the bromination is a one-step reaction wherein the conversion of the 3-methylpyridine 5,6-dialkyl dicarboxylate to the corresponding brominated products with NaBr as source of bromine is greater than 90% in one cycle of reaction (without workup and isolation of the product). With bromine ($Br_2$) as a bromide source, the bromide is decomposed to bromide anion and only 40% is used in the reaction. Therefore, only 50% conversion is obtained (see, e.g., WO 2010/0055139). In the present invention the 80% of the bromide source is used. For obtaining high conversion there is a need for multi-cycle reactions. The multi cycles reaction is resulted in a huge waste of starting material (excess of bromine) and returned workup which are resulted in huge waste.

The bromination reaction with N-bromosuccinimide when using 150% (1.5 eq) brominating agent lead to 70% conversion while using 1.5 eq of NaBr in the present invention the conversion is over 90%. After 6 cycles of oxidant addition, the conversion is 94.0%.

In the present invention the conversion of the bromination reaction is over 90% without need of isolating excess starting material and re-running the reaction (considering total amount of bromo, dibromo, tribromo products).

It was found that the brominated product is stable in the reaction condition and does not decompose. Both product and reactant may undergo ester hydrolysis in aqueous media.

Additionally, unexpectedly when the bromination reaction is performed in the absence of a light and in the presence of radical initiator, mainly brominated products are formed with very limited amount of benzylic oxidation product (see, e.g., Moriyama et al. 2012). It was unexpectedly observed that in order to obtain the oxidation product, both light and OXONE® are required.

Step (ii)

This step enables utilization of polybrominated by products and thus high conversions are possible and no recovery of unreacted starting material is required as is essential when the conversion is low; and higher yields are possible because polybrominated byproducts (mainly dibromo) if not utilized results in lower yields.

Step (iii):

Debromination to the monobrominated intermediate requires dialkylphosphite and a base which is not nucleophilic enough to react with the monobrominated intermediate. Since the monobrominated intermediate is reacted with a tertiary amine or pyridine derivative in the next step, such reactant can be used as a debromination base enabling combination of both steps into a one pot process and sparing the requirement for additional non-nucleophilic base which might be an expensive reagent.

In addition, in step iii wherein the scavenger, e.g. methyl acetate, is used the condition of the reaction are mild and there is no need for high temperature or pressure (closed vessel) to obtain the ether product.

In a process for preparing the compound having the structure:

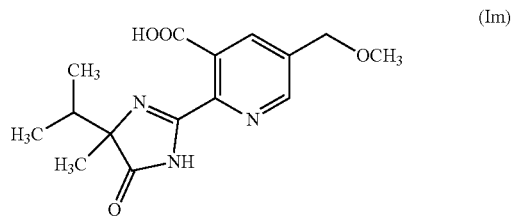 [SMILES: COCc1cnc(C2=NC(C)(C(C)C)C(=O)N2)c(C(=O)O)c1]

which comprises converting a dialkyl-3-methylpyridine-5,6-dicarboxylate to a compound having the structure:

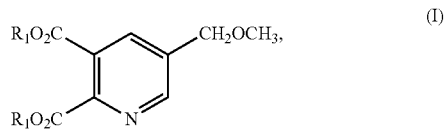

wherein each occurrence of $R_1$ is $C_1$-$C_4$ alkyl, the improvement comprising converting the dialkyl-3-methylpyridine-5,6-dicarboxylate to the compound of formula (I) by the process according to any embodiments of the present invention.

In some embodiments, a process for preparing the compound having the structure:

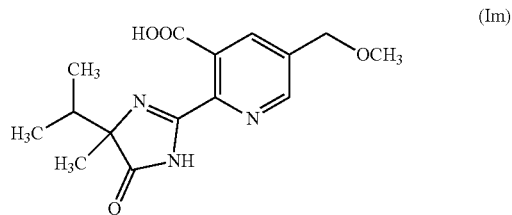 [SMILES: COCc1cnc(C2=NC(C)(C(C)C)C(=O)N2)c(C(=O)O)c1]

which comprises
(a) preparing the compound of formula (I):

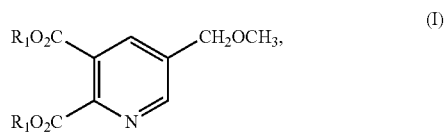

wherein each occurrence of $R_1$ is $C_1$-$C_4$ alkyl, according to any embodiments of the present invention.

In some embodiments, the process further comprising:
(b) converting the compound of formula (I) to the compound of formula (Im).

In some embodiments, the process further comprising:
(b) converting the diester compound of formula (I) to the corresponding anhydride;
(c) reacting the anhydride with 2-amino-2,3-dimethylbutanenitrile followed by base-catalyzed condensation to form the compound of formula (Im).

In some embodiments, the process further comprising:
(b) converting the diester compound of formula (I) to the corresponding anhydride;
(c) reacting the anhydride with 2-amino-2,3-dimethylbutanenitrile followed by acid catalyzed hydrolysis of the nitrile to primary amide followed by base-catalyzed condensation to form the compound of formula (Im).

In some embodiments, the process further comprising:
(b) reacting the diester compound of formula (I) with 2-amino-2,3-dimethylbutyramide to form the compound of formula (Im).

In some embodiments, the process further comprising:
(b) reacting the diester compound of formula (I) with 2-amino-2,3-dimethylbutyramide in the presence of base to form the compound of formula (Im).

In some embodiments, the process further comprising:
(b) reacting the diester compound of formula (I) with 2-amino-2,3-dimethylbutyramide in the presence of base; and
(c) an acidic workup to form the compound of formula (Im).

In some embodiments, a process for preparing the compound having the structure:

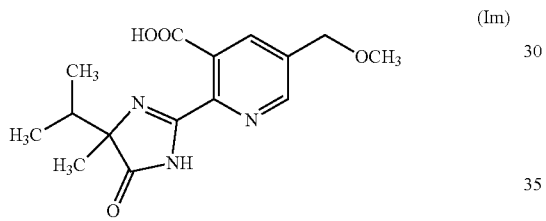

(Im)

which comprises
(a) converting the diester compound of formula (I):

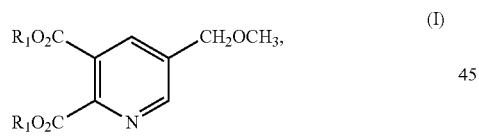

(I)

wherein each occurrence of $R_1$ is $C_1$-$C_4$ alkyl, prepared according to any embodiments of the present invention, to the corresponding diacid under hydrolysis condition;
(b) converting the diacid product of step (a) to the anhydride having the structure:

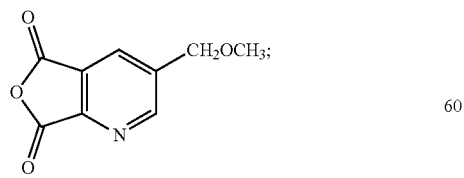

(c) reacting the anhydride product of step (b) with 2-amino-2,3-dimethylbutanenitrile to form the compound having the structure:

(d) reacting the product of step (c) with acid to form the compound having the structure:

(e) reacting the product of step (d) with base to form the compound of formula (Im).

In some embodiments, a process for preparing the compound having the structure:

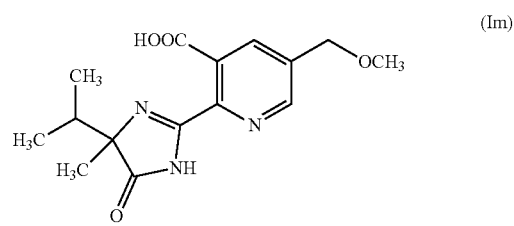 [SMILES: COCc1cnc(C2=NC(C)(C(C)C)C(=O)N2)c(C(=O)O)c1]

(Im)

which comprises
(a) converting the diester compound of formula (I):

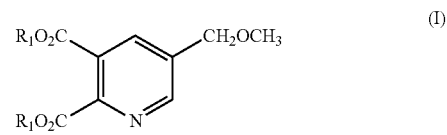

(I)

wherein each occurrence of $R_1$ is $C_1$-$C_4$ alkyl, prepared according to any embodiments of the present invention, to the corresponding diacid under hydrolysis condition;
(b) converting the diacid product of step (a) to the anhydride having the structure:

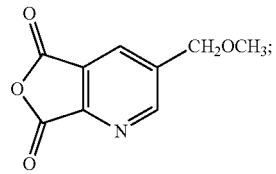

(c) reacting the anhydride product of step (b) with 2-amino-2,3-dimethylbutanenitrile to form the compound having the structure:

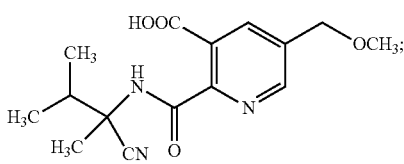 [SMILES: COCc1cnc(C(=O)NC(C)(C#N)C(C)C)c(C(=O)O)c1]

(c) reacting the anhydride product of step (b) with 2-amino-2,3-dimethylbutyramide to form the compound having the structure:

(d) reacting the product of step (c) with base to form the compound of formula (Im).

In some embodiments, the use of the compound of formula (I) as prepared according to any embodiments of the present invention for producing Imazamox.

A process for converting the compound having the structure of formula (I):

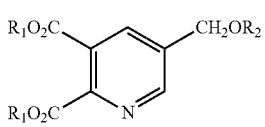

wherein
each occurrence of $R_1$ is a $C_1$-$C_4$ alkyl; and
$R_2$ is $C_1$-$C_4$ alkyl, to the corresponding herbicide having the formula:

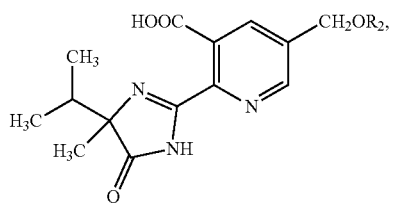

is described in the following: U.S. Pat. No. 5,973,154, US 2011/0245506 A1, WO 2010/055042 A1, WO 2010/066669 A1 and/or EP 0 166 907, the contents of each of which are hereby incorporated by reference.

A process for converting the compound having the structure of formula (I):

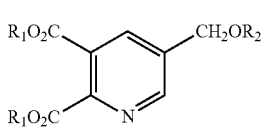

wherein
each occurrence of $R_1$ is a $C_1$-$C_4$ alkyl; and
$R_2$ is methyl, to the corresponding herbicide having the formula:

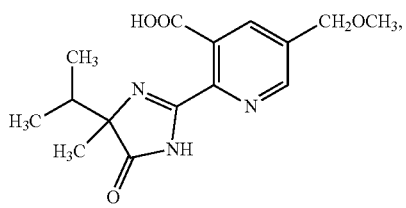

is described in the following: U.S. Pat. No. 5,973,154, US 2011/0245506 A1, WO 2010/055042 A1, WO 2010/066669 A1 and/or EP 0 166 907, the contents of each of which are hereby incorporated by reference.

The present reactions occur under reaction conditions sufficient to produce the desired compound. Such conditions, e.g. temperature, time, molarity, etc., may be varied by one of ordinary skill in the art based on the methods and protocols described herein.

Where a range is given in the specification it is understood that the range includes all integers and 0.1 units within that range, and any sub-range thereof. For example, a range of 77 to 90% is a disclosure of 77, 78, 79, 80, and 81% etc.

As used herein, "about" with regard to a stated number encompasses a range of +one percent to −one percent of the stated value. By way of example, about 100 mg/kg therefore includes 99, 99.1, 99.2, 99.3, 99.4, 99.5, 99.6, 99.7, 99.8, 99.9, 100, 100.1, 100.2, 100.3, 100.4, 100.5, 100.6, 100.7, 100.8, 100.9 and 101 mg/kg. Accordingly, about 100 mg/kg includes, in an embodiment, 100 mg/kg.

It is understood that where a parameter range is provided, all integers within that range, and tenths thereof, are also provided by the invention.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n−1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

The invention is illustrated by the following examples without limiting it thereby.

EXPERIMENTAL SECTION

Example 1

Preparation of Dimethyl 5, 6 dicarboxylate-3-pyridinyl Methyl Bromide Mixture of the Formula (IIa-c)

3-methylpyridine 5, 6-dimethyl dicarboxylate (286.8 mmol, 60 gr) is heated until completed melted and added to 210 mL 1,2 dichloroethane. AIBN (3.1 mmol, 0.6 gr) is added to the reaction mixture followed by 17.3% NaBr solution in water (118.7 mmol, 70.6 gr). The pH is adjusted to 1.5-2.0 using 98% $H_2SO_4$. The reaction is stirred at 70-75° C. while adding 169.8 gr 19.3% OXONE® (3.4% $H_2SO_4$ solution, 106.6 mmol $KHSO_5$) over 30 min. The solution becomes colored. The solution is refluxed for 2 hr then cooled to 25° C. The aqueous phase is discarded.

An additional portion of AIBN (3.1 mmol, 0.6 gr) is added to the reaction mixture followed by an additional portion of 17.3% NaBr solution (118.7 mmol, 70.6 g). The pH is adjusted to 1.5-2.0 using 98% $H_2SO_4$. The reaction is stirred at 70-75° C. while adding an additional 169.8 gr 19.3% OXONE® (3.4% $H_2SO_4$ solution, 106.6 mmol) over 30 min. The solution becomes colored. The solution is refluxed for 2 hr then cooled to 25° C. The aqueous phase is discarded.

A third portion of AIBN (3.1 mmol, 0.6 gr) is added to the reaction mixture followed by a third portion of 17.3% NaBr solution (118.7 mmol, 70.6 g). The pH is adjusted to 1.5-2.0 using 98% $H_2SO_4$. The reaction is stirred at 70-75° C. while adding an additional 169.8 gr 19.3% OXONE® (3.4% $H_2SO_4$ solution, 106.6 mmol) over 30 min. The solution becomes colored. The solution is refluxed for 2 hr then cooled to 25° C. The aqueous phase is discarded.

A fourth portion of AIBN (3.1 mmol, 0.6 g) is added to the reaction mixture followed by a fourth portion of 17.3% NaBr solution (118.7 mmol, 70.6 g). The reaction is stirred at 70-75° C. while adding an additional 169.8 gr 19.3% OXONE® (3.4% $H_2SO_4$ solution, 106.6 mmol) over 30 min. The solution becomes colored. The solution is refluxed for 2 hr then cooled to 25° C. The aqueous phase is discarded A fifth portion of AIBN (3.1 mmol, 0.6 g) is added to the reaction mixture followed by a fifth portion of 17.3% NaBr solution (118.7 mmol, 70.6 g). The reaction is stirred at 70-75° C. while adding an additional 169.8 gr 19.3% OXONE® (3.4% $H_2SO_4$ solution, 106.6 mmol) over 30 min. The solution becomes colored. The solution is refluxed for 2 hr then cooled to 25° C. The aqueous phase is discarded.

A sixth portion of AIBN (3.1 mmol, 0.6 g) is added to the reaction mixture followed by a sixth portion of 17.3% NaBr solution (118.7 mmol, 70.6 g). The reaction is stirred at 70-75° C. while adding an additional 169.8 gr 19.3% OXONE® (3.4% $H_2SO_4$ solution, 106.6 mmol) over 30 min. The solution becomes colored. The solution is refluxed for 2 hr then cooled to 25° C. The aqueous phase is discarded. The organic phase is washed with 420 g 5% $NaHCO_3$. The organic phase is washed with 420 g saturated NaCl solution. The organic phase is dried over MgSO4 and filtrated. The solvent is concentrated under reduced pressure to dryness to obtain 91.4 gr viscous brown oil 96.3% conversion (mono di and three brominated products)

Treatment by sodium bisulfite: addition of 20% sodium bisulfite solution until complete neutralization is obtained (indicated by potassium iodide indicator paper).

TABLE 1

| | Conversions per cycle [step (i)]. | | | |
|---|---|---|---|---|
| Cycle# | MPDC-DME | BPDC-DME | DPDC-DME | TPDC-DME |
| 1 | 73.5% | 23.7% | 0.9% | ND |
| 2 | 50.1% | 44.1% | 3.8% | ND |
| 3 | 30.1% | 57.4% | 9.9% | 0.8% |
| 4 | 16.8% | 61.4% | 18.3% | 1.0% |
| 5 | 7.9% | 57.8% | 29.5% | 1.9% |
| 6 | 2.9% | 48.8% | 41.4% | 3.7% |

Reaction with Light in Absence of Initiator

Diethyl-3-methylpyridine-5,6-dicarboxylate (5.6 g, 23.6 mmol) is added to 1, 2-dichloroethane (40 ml). To the obtained solution KBr (3.4 g, 28.6 mmol) was added. OXONE® (14.0 GR, 45.5 mmol; $KHSO_5$) is added followed by water (40 g) and the reaction mixture is illuminated by tungsten lamp for 7.5 hr.

TABLE 2

| Conversions by light [step (i)]. 1.2eq. KBr, 1.9eq. OXONE ®, 7 hr, 30-40° C. | | | |
|---|---|---|---|
| MPDC | BPDC | DPDC | CPDC |
| 6.8% | 63.9% | 25.3% | 2.3% |

Preparation of dimethyl-5, 6 dicarboxylate-3-pyridyl Methyl Ammonium Salt of the Formula (III)

The brominated mixture IIa-c (88.4 g) is diluted with 470 ml 1,2-DCE. The solution is cooled to 0-5° C. and DEP (136.9 mmol, 18.9 g) is added followed by 33% $(CH_3)_3N$ (441.0 mmol, 79.0 g) in EtOH. The reaction mixture is stirred for 0.5 hr at 0-5° C. than heated to 25° C. for 1 hr (the reaction is stirred for 6 hr in case that the reaction still not finished adding additional DEP (13.8 mmol, 11.9 g) at 0-5° C., stirring at 25° C. for 1 hr and then at reflux for 1 hr).

The resulting precipitate is dried under vacuum at 50° C. to obtain 77.0 g (221.8 mmol) (79.9% yield).

Preparation of dimethyl-5,6-dicarboxylate-3-methoxy Methyl Pyridine (I)

Methyl acetate (1.35 mmol, 1.0 g) and of sodium methoxide solution (30% in methanol) (23.88 mmol, 4.3 g) are added to methanol (20 g) under $N_2$ atmosphere. The resulting mixture is heated to reflux (60-65° C.) for 1.0 hr then cooled to 25° C. at which point compound III is added 12.82 mmol, 5.0 g, 89%). The reaction mixture is stirred at reflux (60-65° C.) for 3 hr then cooled to 10-15° C. while acetic acid (1.45 g) is added dropwise over 10 mins. The solvent is concentrated under reduced pressure to dryness. Toluene (40 ml) is added and washed with 20 gr water. The aqueous wash is extracted with 30 ml toluene and the combined organic phases are washed by 20 gr water. The solvent is concentrated under reduced pressure to obtain 2.7 g of desired product (87.2% yield, 99.0% purity).

Discussion

There is a need to develop an improved synthetic process for producing the dialkyl-3-alkoxymethyl-5,6-dicarboxylate intermediate which is useful in synthesizing the herbicide Imazamox.

The process described herein is carried out in ambient pressure, with easily handled material, in a process that is highly efficient, low-cost, and environmentally friendly. These advantages are not exhibited by any current methods. It has been found that the synthesis of dimethyl 5-(methoxymethyl)pyridine-2,3-dicarboxylate (and related dialkyl-3-alkoxymethyl-5,6 dicarboxylates) in the specific steps described here can significantly improve the conversion and isolated yield of the desired product.

REFERENCES

Kennedy, R. J. et al. (1960) The Oxidation of Organic Substances by Potassium Peroxymonosulfate. J. Org. Chem. 25, 1901.
Liu, Y. et al. (2001) An Efficient Method for the Preparation of Benzylic Bromides. Synthesis 14, 2078.
Moriyama, K. et al. (2014) Selective oxidation of alcohols with alkali metal bromides as bromide catalysts: experimental study of the reaction mechanism. Org. Lett. 79, 6094.
EP 0 548 532 A1, published Jun. 30, 1993 (Strong).
EP 0 166 907 A2, published Jan. 8, 1986 (American Cyanamid Company).
U.S. Pat. No. 5,760,239, issued Jun. 2, 1998 (Wu et al.).
U.S. Pat. No. 5,973,154, issued Oct. 26, 1999 (Drabb et al.).
US 2011/0245506 A1, published Oct. 6, 2011 (Cortes).
WO 2010/055139 A1, published May 20, 2010 (Gebhardt et al.).
WO 2010/066669 A1, published Jun. 17, 2010 (Rippel).
WO 2010/055042 A1, published May 20, 2010 (Cortes).

What is claimed is:

1. A process for preparing a compound of the formula (I):

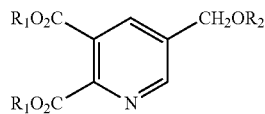

wherein
each occurrence of $R_1$ is a $C_1$-$C_4$ alkyl; and
$R_2$ is $C_1$-$C_4$ alkyl,
comprising the steps of:
(i) reacting a dialkyl-3-methylpyridine-5,6-dicarboxylate with potassium peroxymonosulfate and a halogen metal salt to obtain a mixture comprising the compounds of the formulas IIa, and/or IIb and/or IIc:

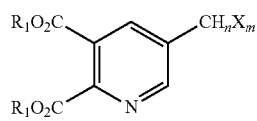

wherein
n=2 and m=1 (IIa), n=1 and m=2 (IIb), or n=0 and m=3 (IIc);
each occurrence of $R_1$ is a $C_1$-$C_4$ alkyl; and
X is a halogen, (ii) reacting the mixture produced in step (i) with an amine to obtain a compound of the formula (III):

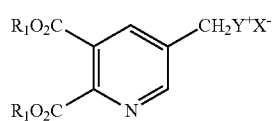

wherein
each occurrence of $R_1$ is a $C_1$-$C_4$ alkyl;
$Y^+$ is

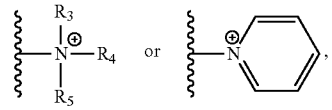

wherein $R_3$, $R_4$ and $R_5$ are each, independently, a $C_1$-$C_6$ alkyl or aryl; and
X is a halogen,
(iii) reacting the product of step (ii) with an alcohol metal base.

2. The process of claim 1, wherein step (i) occurs in the presence of a radical initiator, or the radical reaction is induced by visible light or ultraviolet light or is performed in the presence of visible light or ultraviolet light.

3. The process of claim 2, wherein the radical initiator is azobisisobutyronitrile (AIBN).

4. The process of claim 1, wherein the potassium peroxymonosulfate in step (i) is added to the reaction mixture gradually in two or more portions.

5. The process of claim 1, wherein the reaction is performed in a first suitable solvent selected from dichloromethane, chloroform, 1,2-dichloroethane, perchloroethylene, trichloroethane, chlorobenzene, 2-dichlorobenzene, 3-dichlorobenzene, 4-dichlorobenzene, benzene, carbon tetrachloride or any combination thereof.

6. The process of claim 5, wherein the concentration of potassium peroxymonosulfate in the reaction solution is less than 5% or is less than 1%.

7. The process of claim 5, wherein the concentration of the dialkyl-3-methylpyridine-5,6-dicarboxylate in step (i) relative to the reaction solution is less than 5% and/or the concentration of the halogen metal salt in step (i) relative to the reaction solution is less than 5%.

8. The process of claim 1, wherein in step (ii) the mixture comprising the halogenated compounds of formula IIa-c of step (i) react with the amine in the presence of diethylphosphite, or wherein in step (ii) the dihalogenated and trihalogenated products IIb and IIc of step (i) are converted to the monohalogenated product IIa prior to reaction with the amine.

9. The process of claim 1, wherein the amine in step (ii) is trimethylamine.

10. The process of claim 1, wherein the metal in step (i) and/or (iii) is alkali or earth alkaline.

11. The process of claim 1, wherein the halogen X is bromide, chloride, fluoride or iodide, or wherein the halogen metal salt in step (i) is sodium bromide, or wherein the alcohol in step (iii) is methanol.

12. The process of claim 1, wherein step (iii) is carried out in the presence of a hydroxide scavenger agent, or wherein step (iii) is carried out in the presence of methyl acetate as a hydroxide scavenger agent.

13. The process of claim 1, wherein step (i) produces a mixture of the following compounds:

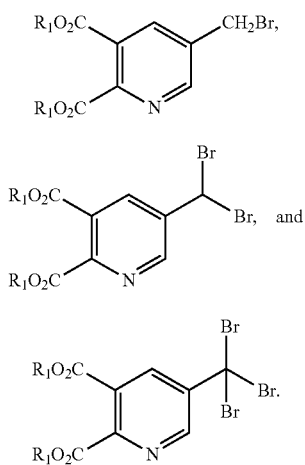

14. The process of claim 1, wherein the compound produced has the structure:

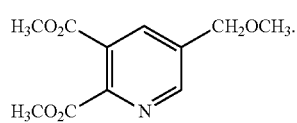

15. The process of claim 1, wherein the potassium peroxymonosulfate source is a triple salt with the formula $KHSO_5 \cdot 0.5KHSO_4 \cdot 0.5K_2SO_4$.

16. The process of claim 1, further comprising a step (i)(a) after step (i) and prior to step (ii) wherein the mixture comprising the compounds IIa-c of step (i) are reacted with a dialkylphosphite so as to therefore covert the compound of the formula IIb-c to the compound of the formula IIa.

17. A process for preparing a mixture comprising compounds of the formula IIa and/or IIb and/or IIc:

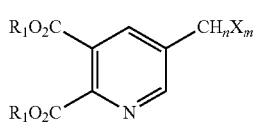

wherein
X is a halogen;
Each occurrence of $R_1$ is $C_1$-$C_4$ alkyl;
n=2 and m=1 (IIa), n=1 and m=2 (IIb) or n=0 and m=3 (IIc), comprising reacting a dialkyl-3-methylpyridine-5,6-dicarboxylate with potassium peroxymonosulfate and a halogen metal salt in the presence of a radical initiator; or a process for preparing the compound of the formula

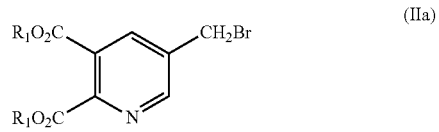

wherein
each occurrence of $R_1$ is a $C_1$-$C_4$ alkyl,
comprising reacting of compounds of formula (IIb-c)

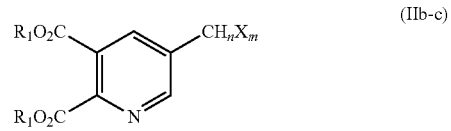

wherein
n=1 and m=2 (IIb), or n=0 and m=3 (IIc);
each occurrence of $R_1$ is a $C_1$-$C_4$ alkyl; and
X is a bromine,
with a dialkylphosphite in the presence of a base so as to therefore obtain the compound of the formula (IIa).

18. A process for preparing compound of the formula (III):

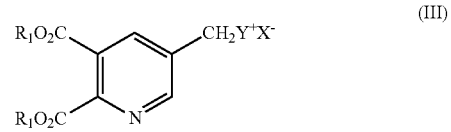

wherein
each occurrence of $R_1$ is a $C_1$-$C_4$ alkyl;
$Y^+$ is

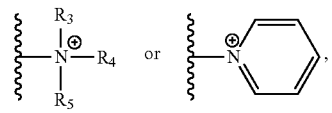

wherein $R_3$, $R_4$ and $R_5$ are each, independently, a $C_1$-$C_6$ alkyl or aryl; and
X is a halogen,
comprising reacting a mixture comprising compounds of the formula IIa and/or IIb and/or IIc:

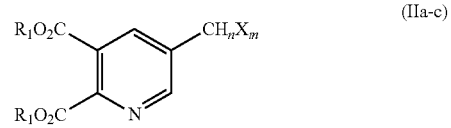

wherein
n=2 and m=1 (IIa), n=1 and m=2 (IIb) or n=0 and m=3 (IIc);
each occurrence of $R_1$ is a $C_1$-$C_4$ alkyl; and
X is a halogen,
with a dialkylphosphite in presence of an amine so as to therefore obtain the compound of the formula (III), or a process for preparing a compound of the formula (I):

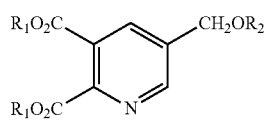

wherein
Each occurrence of $R_1$ is $C_1$-$C_4$ alkyl;
$R_2$ is $C_1$-$C_4$ alkyl,
comprising reacting the compound of formula (III):

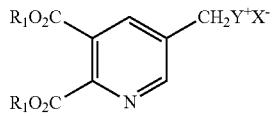

wherein
each occurrence of $R_1$ is a $C_1$-$C_4$ alkyl;
$Y^+$ is

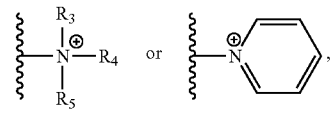

wherein $R_3$, $R_4$ and $R_5$ are each, independently, a $C_1$-$C_6$ alkyl or aryl; and
X is halogen,
with an alcohol metal base in the presence of a hydroxide scavenger agent or with an alcohol metal base which was previously treated with a hydroxide scavenger agent.

19. In a process for preparing the compound having the structure:

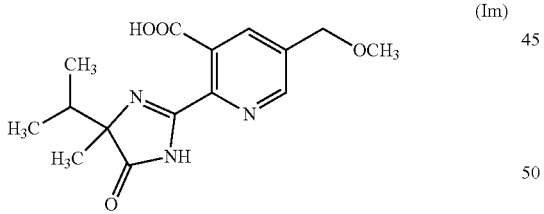

which comprises converting a dialkyl-3-methylpyridine-5,6-dicarboxylate to a compound having the structure:

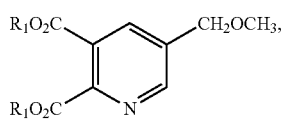

wherein each occurrence of $R_1$ is $C_1$-$C_4$ alkyl, the improvement comprising converting the dialkyl-3-methylpyridine-5,6-dicarboxylate to the compound of formula (I) by the process of claim 1.

20. A process for preparing the compound having the structure:

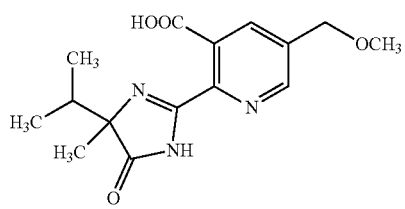

which comprises
(a) preparing the compound of formula (I):

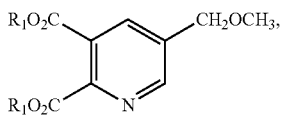

wherein each occurrence of $R_1$ is $C_1$-$C_4$ alkyl, according to the process of claim 1; or
which comprises
(a) converting the diester compound of formula (I):

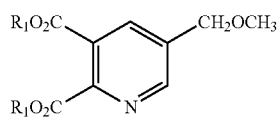

wherein each occurrence of $R_1$ is $C_1$-$C_4$ alkyl, prepared according to process of claim 1, to the corresponding diacid under hydrolysis condition;
(b) converting the diacid product of step (a) to the anhydride having the structure:

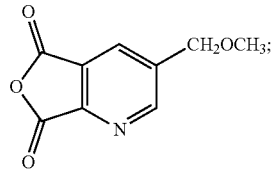

(c) reacting the anhydride product of step (b) with 2-amino-2,3-dimethylbutanenitrile to form the compound having the structure:

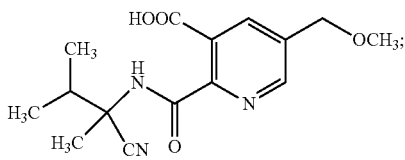 [SMILES: COCc1cnc(C(=O)NC(C)(C#N)C(C)C)c(C(=O)O)c1]

(d) reacting the product of step (c) with acid to form the compound having the structure:
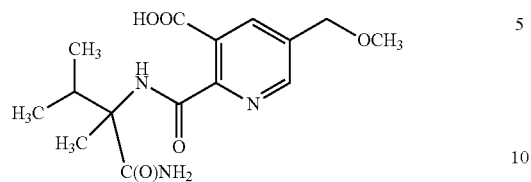
(e) reacting the product of step (d) with base to form the compound of formula (Im).
* * * * *